United States Patent
Blum et al.

(10) Patent No.: US 10,052,195 B2
(45) Date of Patent: Aug. 21, 2018

(54) ADAPTIVE INTRAOCULAR LENS

(75) Inventors: Ronald David Blum, Roanoke, VA (US); Rudy Mazzocchi, Roanoke, VA (US)

(73) Assignee: ELENZA, INC., Roanoke, VA (US)

( * ) Notice: Subject to any disclaimer, the term of this patent is extended or adjusted under 35 U.S.C. 154(b) by 0 days.

(21) Appl. No.: 13/885,366

(22) PCT Filed: Nov. 14, 2011

(86) PCT No.: PCT/US2011/060556
§ 371 (c)(1),
(2), (4) Date: May 14, 2013

(87) PCT Pub. No.: WO2012/067994
PCT Pub. Date: May 24, 2012

(65) Prior Publication Data
US 2013/0245754 A1    Sep. 19, 2013

Related U.S. Application Data

(60) Provisional application No. 61/413,542, filed on Nov. 15, 2010, provisional application No. 61/428,064, (Continued)

(51) Int. Cl.
*A61F 2/16*     (2006.01)

(52) U.S. Cl.
CPC .......... *A61F 2/1624* (2013.01); *A61F 2/1613* (2013.01); *A61F 2/1627* (2013.01);
(Continued)

(58) Field of Classification Search
CPC ............................. A61F 2/1624; A61F 2/1635
See application file for complete search history.

(56) References Cited

U.S. PATENT DOCUMENTS

| | | | |
|---|---|---|---|
| 4,731,078 A | 3/1988 | Stoy et al. | |
| 6,423,001 B1 * | 7/2002 | Abreu ................. | A61B 3/1241 |
| | | | 600/399 |

(Continued)

FOREIGN PATENT DOCUMENTS

| | | |
|---|---|---|
| JP | 62-151824 | 7/1987 |
| JP | 11-276509 A | 10/1999 |

(Continued)

OTHER PUBLICATIONS

International Preliminary Report on Patentability received in corresponding International Application No. PCT/US2011/060556, dated Oct. 15, 2013, 12 pages.

(Continued)

*Primary Examiner* — David Isabella
*Assistant Examiner* — Christine Nelson
(74) *Attorney, Agent, or Firm* — Foley & Lardner LLP

(57) ABSTRACT

An implantable ophthalmic device with flexible, fluid-filled membranes provide dynamically variable optical power to restore lost accommodation in individuals suffering from presbyopia or aphakia without moving parts or reducing the amount of transmitted light. Actuating the device causes the fluid-filled membrane to change curvature, which produces a corresponding change in optical power. For instance, squeezing the edge of the membrane causes the center of the membrane to bulge by an amount proportional to the squeezing force. Alternatively, heating or applying a voltage to the membrane may cause the liquid in the membrane to undergo a phase transition accompanied by a corresponding change in volume that causes the membrane to inflate so as to change the optical power of the device.

20 Claims, 6 Drawing Sheets

Related U.S. Application Data filed on Dec. 29, 2010, provisional application No. 61/428,079, filed on Dec. 29, 2010.

(52) U.S. Cl.
CPC .......... *A61F 2/1635* (2013.01); *A61F 2/1648* (2013.01); *A61F 2210/008* (2013.01); *A61F 2210/009* (2013.01)

(56) References Cited

U.S. PATENT DOCUMENTS

| | | | |
|---|---|---|---|
| 6,935,743 B2 * | 8/2005 | Shadduck | A61F 2/1613 351/159.04 |
| 7,261,736 B1 * | 8/2007 | Azar | A61F 2/08 351/159.08 |
| 7,926,940 B2 | 4/2011 | Blum et al. | |
| 2003/0060878 A1 | 3/2003 | Shadduck | |
| 2005/0143814 A1 | 6/2005 | Esch et al. | |
| 2007/0118216 A1 | 5/2007 | Pynson | |
| 2007/0129798 A1 * | 6/2007 | Chawdhary | A61F 2/1613 623/6.13 |
| 2007/0260307 A1 | 11/2007 | Azar | |
| 2008/0306589 A1 | 12/2008 | Donitzky et al. | |
| 2009/0264998 A1 * | 10/2009 | Mentak | A61F 2/1613 623/6.37 |
| 2010/0004741 A1 | 1/2010 | Gupta et al. | |
| 2010/0057202 A1 * | 3/2010 | Bogaert | A61F 2/1618 623/6.27 |
| 2010/0228344 A1 | 9/2010 | Shadduck | |
| 2011/0015733 A1 | 1/2011 | Schnell et al. | |

FOREIGN PATENT DOCUMENTS

| | | |
|---|---|---|
| JP | 2006-518222 A | 8/2006 |
| JP | 2006-527014 A | 11/2006 |
| JP | 2007-089810 A | 4/2007 |
| JP | 2008-541805 A | 11/2008 |
| JP | 2008-543350 | 12/2008 |
| JP | 2010-517081 A | 5/2010 |
| WO | WO-2004/054471 A2 | 7/2004 |
| WO | WO-2010/004094 A1 | 1/2010 |
| WO | WO-2011/153158 A1 | 12/2011 |
| WO | WO-2011/163080 A1 | 12/2011 |
| WO | WO-2011/163559 A1 | 12/2011 |
| WO | WO-2012/033752 A1 | 3/2012 |
| WO | WO-2012/037019 A1 | 3/2012 |

OTHER PUBLICATIONS

International Search Report and Written Opinion received in PCT/US2011/060556 dated Feb. 28, 2012.
Supplementary Search Report in corresponding European application No. 11841019.0 dated Feb. 17, 2015, 6 pages.
Japanese Office Action in corresponding Japanese application No. 2013-538967 dated Sep. 1, 2015, with English Translation, 9 pages.
Office Action dated Aug. 9, 2016, received in corresponding Japanese Application No. 2013-538967 (4 pages) and English translation (4 pages).
Office Action dated Nov. 14, 2017, received in corresponding Japanese application No. 2016-239111 (3 pages) and English translation (2 pages).
Examination Report dated Mar. 2, 2018 received in corresponding Canadian Application No. 2,817,017, 4 pages.
Office Action dated Apr. 3, 2018, received in corresponding Japanese application No. 2016-239111, (5 pages) and English translation (4 pages).

* cited by examiner

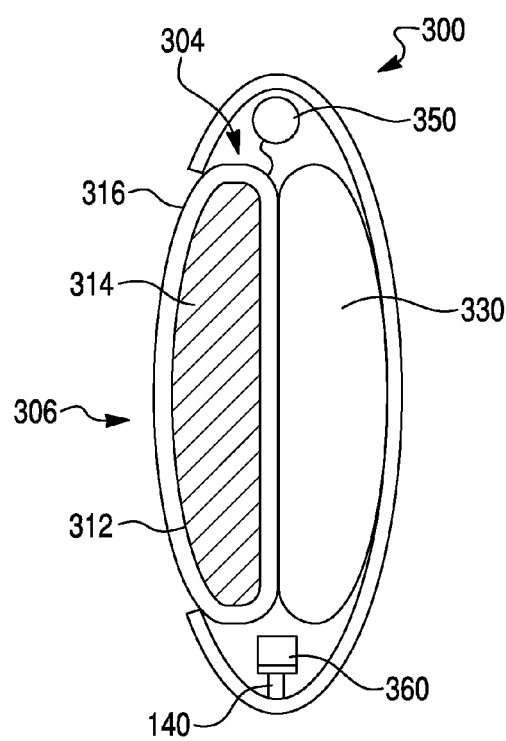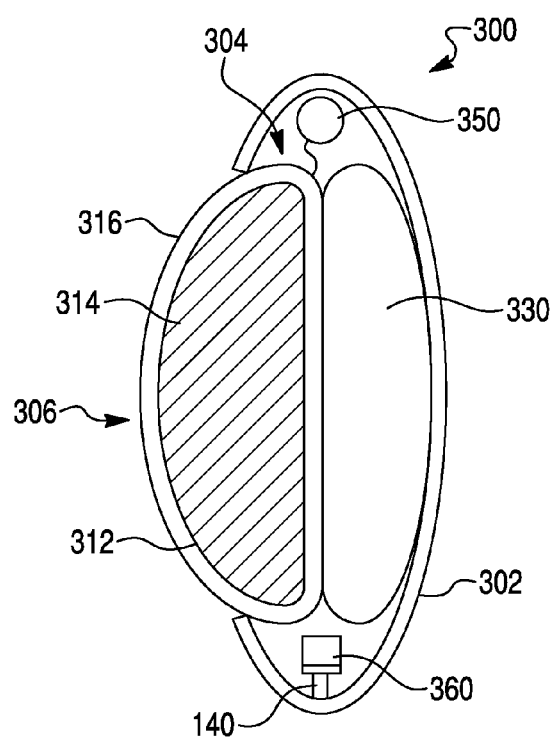

ADAPTIVE INTRAOCULAR LENS

CROSS REFERENCE TO RELATED APPLICATIONS

The present application is a National Stage of International Application No. PCT/US2011/060556 filed on Nov. 14, 2011, which claims the benefit of U.S. Provisional Patent Application No. 61/413,542 filed on Nov. 15, 2010, U.S. Provisional Patent Application No. 61/428,064 filed on Dec. 29, 2010, and U.S. Provisional Patent Application No. 61/428,079 filed on Dec. 29, 2010, the entire disclosures of all of which are incorporated herein by reference.

BACKGROUND

There are two major conditions that affect an individual's ability to focus on near and intermediate distance objects: presbyopia and pseudophakia. Presbyopia is the loss of accommodation of the crystalline lens of the human eye that often accompanies aging. In a presbyopic individual, this loss of accommodation first results in an inability to focus on near distance objects and later results in an inability to focus on intermediate distance objects. It is estimated that there are approximately 90 million to 100 million presbyopes in the United States. Worldwide, it is estimated that there are approximately 1.6 billion presbyopes.

The standard tools for correcting presbyopia are reading glasses, multifocal ophthalmic lenses, and contact lenses fit to provide monovision. Reading glasses have a single optical power for correcting near distance focusing problems. A multifocal lens is a lens that has more than one focal lengths (i.e., optical power) for correcting focusing problems across a range of distances. Multifocal optics are used in eyeglasses, contact lenses, and intra-ocular lenses (IOLs). Multifocal ophthalmic lenses work by means of a division of the lens's area into regions of different optical powers. Multifocal lenses may be comprised of continuous surfaces that create continuous optical power as in a Progressive Addition Lens (PAL). Alternatively, multifocal lenses may be comprised of discontinuous surfaces that create discontinuous optical power as in bifocals or trifocals. Contact lenses fit to provide monovision are two contact lenses having different optical powers. One contact lens is for correcting mostly far distance focusing problems and the other contact lens is for correcting mostly near distance focusing problems.

Pseudophakia is the replacement of the crystalline lens of the eye with an IOL, usually following surgical removal of the crystalline lens during cataract surgery. For all practical purposes, an individual will get cataracts if he or she lives long enough. Furthermore, most individuals with cataracts will have a cataract operation at some point in their lives. It is estimated that approximately 1.2 million cataract surgeries are performed annually in the United States. In a pseudophakic individual, the absence of the crystalline lens causes a complete loss of accommodation that results in an inability to focus on either near or intermediate distance objects.

Conventional IOLs are monofocal, spherical lenses that provide focused retinal images for far objects (e.g., objects over two meters away). Generally, the focal length (or optical power) of a spherical IOL is chosen based on viewing a far object that subtends a small angle (e.g., about seven degrees) at the fovea. Unfortunately, because a monofocal IOL has a fixed focal length, it cannot mimic or replace the eye's natural accommodation response. Fortunately, ophthalmic devices with electro-active elements, such as liquid crystal cells, can be used to provide variable optical power as a substitute for the accommodation of a damaged or removed crystalline lens. For example, electro-active elements can be used as shutters that provide dynamically variable optical power as disclosed in U.S. Pat. No. 7,926,940 to Blum et al., which is incorporated herein by reference in its entirety.

SUMMARY

Embodiments of the present invention include an implantable ophthalmic device and associated method of changing the optical power of an implantable ophthalmic device. One exemplary implantable ophthalmic device includes a lens formed of a flexible membrane defining a sealed cavity and a fluid disposed within the sealed cavity. The exemplary implantable ophthalmic device also includes an actuator that is configured to alter a shape of the flexible membrane so as to change an optical power of the lens (e.g., by up to about 3.5 Diopters), possibly in response to detection of an accommodative stimulus by a sensor.

In at least one example, the flexible membrane forms an aspheric lens element having a negative spherical aberration. The flexible membrane can have a thickness of about 2 microns to about 100 microns and define the sealed cavity to have a thickness of about 0.5 microns to about 5 microns. The pressure inside the sealed cavity may be about 2 mm Hg to 50 mm Hg, and the fluid inside the sealed cavity may have a refractive index of about 1.40 to about 1.80 (e.g., about 1.46 to about 1.65).

In another example, the lens in the implantable ophthalmic device further includes a static lens element (e.g., with an optical power of about 4 Diopters to about 30 Diopters) in optical communication with the flexible membrane. The flexible membrane has a first elastic modulus, and the static lens element has a second elastic modulus that is greater than the first elastic modulus. In some cases, the second elastic modulus is at least about two times greater than the first elastic modulus (e.g., the second elastic modulus can be about ten times to about fifty times greater than the first elastic modulus, but no more than about one-thousand times greater than the first elastic modulus).

The actuator in an illustrative implantable ophthalmic device may be configured to elastically deform at least part of a circumferential portion of the flexible membrane so as to change a radius of curvature of at least part of the flexible membrane to provide the change in optical power. For example, the actuator may include: a first magnetic layer disposed on a first side of the flexible membrane, a second magnetic layer disposed on a second side of the flexible membrane, and an electrode configured to apply a current to the first magnetic layer so as to induce a magnetic field that attracts the second magnetic layer to the first magnetic layer. Attraction of the second magnetic layer to the first magnetic layer causes elastic deformation of at least part of the circumferential portion of the flexible membrane.

Alternatively, the actuator in an illustrative implantable ophthalmic device may be configured to induce a change in molar volume of the fluid (e.g., of about 0.1% to about 0.4%) so as to change a radius of curvature of at least part of the flexible membrane to provide the change in optical power. In one instance, the actuator induces the change in molar volume by heating or cooling the fluid so as to cause the fluid to undergo a phase transition. In another instance, the actuator induces the change in molar volume by applying an electric field to the fluid so as to cause the fluid to undergo a phase transition, e.g., through resistive heating of the fluid or changing the fluid's phase transition temperature.

The fluid in the implantable ophthalmic device may include a liquid crystal material that undergoes a phase transition from a first phase to a second phase at a temperature of between about 35° C. and about 45° C., and the actuator may be configured to cause the liquid crystal material to undergo the phase transition so as to change the optical power of the lens. The phase transition can be a first-order phase transition, e.g., from a first phase to a second phase at a first temperature. The liquid crystal material may further undergo another phase transition from the second phase to the first phase at a second temperature different than the first temperature. The liquid crystal material can be substantially transparent in both the first phase and the second phase.

An exemplary implantable ophthalmic device may also include a sensor configured to detect an accommodative stimulus and to provide a signal for triggering the actuator in response to the accommodative stimulus. The sensor may provide the signal by detecting a physiological response of an eye, detecting an ambient light level, and generating the signal in response to the ambient light level and to a presence of the physiological response. The sensor may be coupled to a processor that receives the signal and triggers the actuator in response to the signal and a power supply configured to power the electronic components in the implantable ophthalmic device. The components may be encapsulated in a hermetically sealed housing, or capsule, that also encloses the lens and the actuator. The housing may also include another fluid (e.g., saline) to reduce reflection from components within the housing.

Another exemplary implantable ophthalmic device includes a sealed housing that encapsulates a static lens element, a flexible lens element defining a sealed cavity, a fluid inside the sealed cavity, and an actuator that configured to compress at least a peripheral portion of the flexible membrane. Alternatively, the fluid disposed within the cavity includes a liquid crystal material that undergoes a first-order phase transition at a temperature of about 35° C. to about 45° C., and the actuator is configured to cause the liquid crystal material to undergo the phase transition.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

FIGS. 3A and 3B are side views of an inventive adaptive implantable ophthalmic device with a thermally or electrically actuated fluid-filled membrane in an unactuated state (FIG. 3A) and an actuated state (FIG. 3B).

DETAILED DESCRIPTION

Figures 1A, 1B:
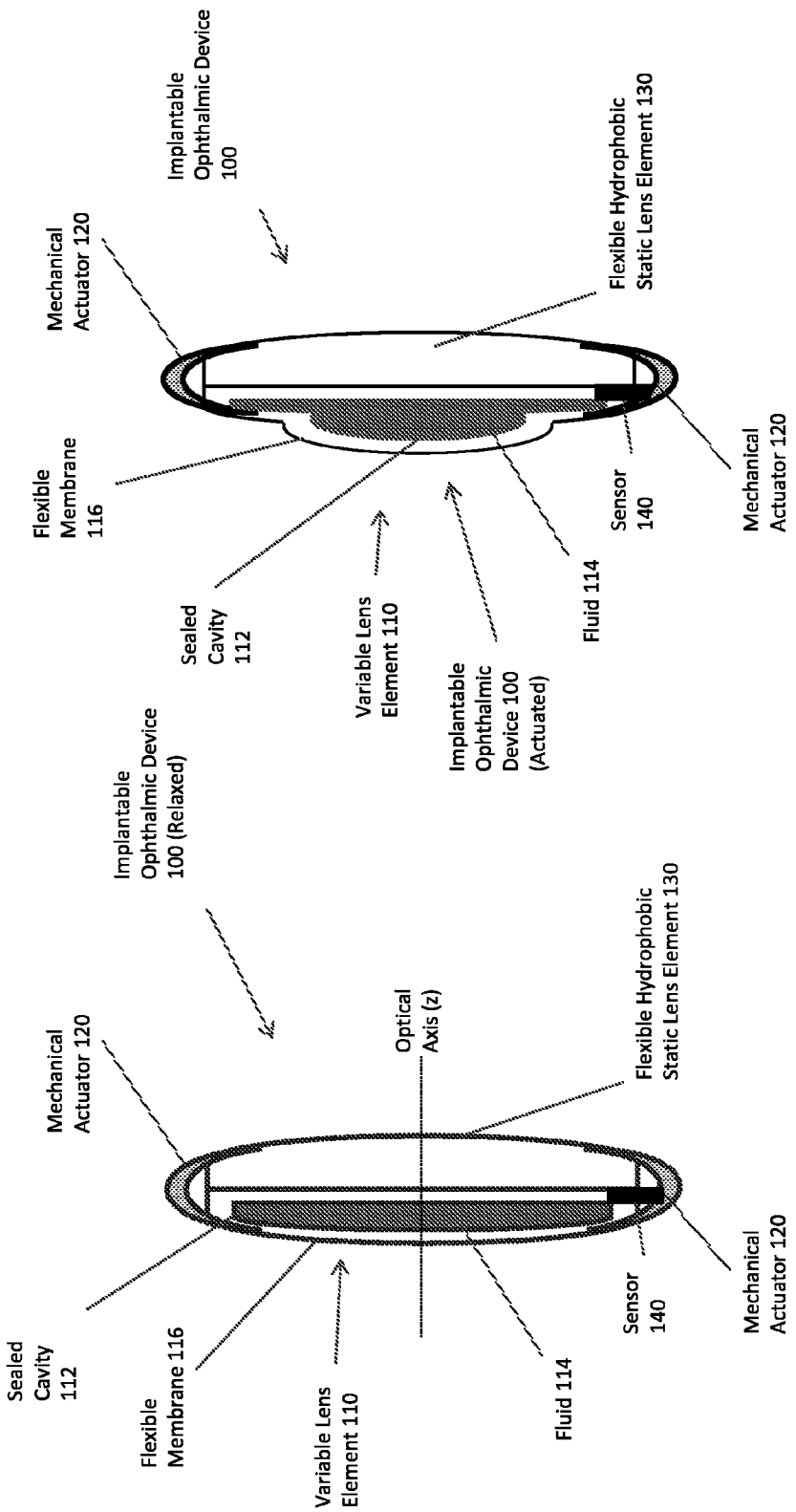
FIGS. 1A and 1B are side views of an inventive adaptive implantable ophthalmic device with actuators that mechanically deform a fluid-filled membrane in an unactuated state (FIG. 1A) and an actuated state (FIG. 1B).

Presently preferred embodiments of the invention are illustrated in the drawings. An effort has been made to use the same or like reference numbers to refer to the same or like parts.

Static intraocular lenses (IOLs), which are generally implanted after cataract extraction, generally cannot provide uncompromised vision at all distances. Mono-focal static IOLs are designed and selected to provide excellent vision at optical infinity, but must be used with reading glasses or bifocal spectacles for uncompromised near and intermediate vision. A multifocal static IOL provides good vision at far and near distances, but produces double images on the retina at all object distances, leading to loss of contrast. It may also cause sensations of ghosting, double images, flare, and glare, all due to the fact that part of one part of the multifocal optic is designed to provide best focus at far distance and another part is designed to provide best focus at near distance.

There have been attempts to create a passive accommodative IOL that mimic the behavior of the crystalline lens. Such a passive accommodative IOL includes a flexible lens whose optical power changes when the lens is squeezed circumferentially, just like the crystalline lens. When implanted, capsular contraction and dilation are supposed to change the optical power of the passive accommodative IOL. Unfortunately, capsular forces have been clinically proven to be unreliable for accommodation and dis-accommodation using passive IOLs.

A typical active accommodative IOL includes an actuator that changes the optical power or position of an optical element in response to a signal from a sensor. When the sensor detects an accommodative stimulus, it sends a signal to the actuator, which responds to the signal by changing the size or shape of an electro-active aperture or moving a lens along the eye's optical axis to change the accommodative IOL's effective optical power or depth of field. The actuator changes the aperture back to its original size and shape or moves the lens back to its original position when the need for an accommodative response ends. Although accommodative IOLs with electro-active apertures and moving lenses both work better than static IOLs and passive accommodative IOLs, they suffer from drawbacks as well. A moving lens may become immobile if it is captured by avascular tissue fibrils, which are the products of chronic inflammation or proliferation of cortical or nuclear remnants of the excised crystalline lens. Immobility is less likely to hinder operation of an electro-active aperture, but closing an electro-active aperture necessarily involves reducing the amount of light incident on the retina.

Embodiments of the inventive implantable ophthalmic devices provide the advantage of active accommodative IOLs without the drawbacks associated with moving parts or apertures. In one example, an inventive implantable ophthalmic device includes a flexible lens element that defines a sealed cavity, which contains a transparent fluid. One or more actuators change the radius of curvature of at least part of the flexible lens element (e.g., by squeezing, heating, or applying an electromagnetic field to the fluid) in response to a signal indicating that a sensor has detected an accommodative stimulus.

Inventive implantable ophthalmic devices may take the form of IOLs, intraocular optics (IOOs), corneal inlays, and corneal onlays. An inventive implantable ophthalmic device may be inserted or implanted in the anterior chamber or posterior chamber of the eye, into the capsular sac, or the stroma of the cornea (similar to a corneal inlay), or into the epithelial layer of the cornea (similar to a corneal onlay), or within any anatomical structure of the eye. An inventive implantable ophthalmic device may have one or more thin, hinge-like sections that allow the implantable ophthalmic device to be folded before implantation and unfolded once positioned properly in a patient's eye. When implanted, partially transparent and opaque elements, such as the sensor, processor, and battery, may be disposed out of the patient's line of sight (e.g., in the vicinity of the haptic/optic junction).

In cases where the implantable ophthalmic device is an IOL, the IOL may have at least one static optical power provided by a curved surface (e.g., the static optical element 130 of FIGS. 1A and 1B) or a graded index profile. Alternatively, the implantable ophthalmic device may be an IOO, which has little to no optical power except when actuated as described herein. In some illustrative devices, the actuators and flexible lens element may provide a continuous range of focus between the fixed or static corrective powers of the ophthalmic lens.

Optical Power Variation by Mechanical Actuation of Flexible Membranes

FIGS. 1A and 1B show an implantable ophthalmic device 100 that includes a variable lens element 110 that provides variable optical power in response to an accommodative stimulus or trigger. The lens element 110 may be a plano-convex asphere with variable negative spherical aberration as described in PCT/US2011/038597 filed May 31, 2011, and entitled, "Intermediate Vision Provided by an Aspheric IOL with an Embedded Dynamic Aperture," which is incorporated herein by reference in its entirety. Its effective diameter (i.e., clear aperture) varies from a minimum size of about 3.0 mm to a maximum size of about 7.0 mm. The implantable ophthalmic device 100 has an edge thickness of about 0.1 mm to about 1.5 mm (e.g., about 0.3 mm to about 0.7 mm).

The variable lens element 110 is formed of a flexible membrane 116, which is made of a transparent biocompatible material, such as an impermeable flexible polymer. Suitable materials include, but are not limited to polyimide, poly(methyl methacrylate) (PMMA), kynar, polyvinyl fluoride (PVF), and polyvinylidene fluoride (PVDF). The flexible membrane may be about 2-100 microns thick (e.g., about 5-50 microns thick) and includes a circumferential bonded zone that is about 0.5 microns to about 5 microns thick (e.g., about 1-2 microns thick) that seals the flexible membrane 116 to form a sealed cavity 112 about 100 microns thick with an area of about 15 mm$^2$ (for a volume of about 1.5 mm$^3$). The posterior (unbonded) surface of the flexible membrane 116 is designed to overcome vitreous pressure and to make secure contact with the posterior capsule of the eye in order to inhibit growth of cortical and epithelial cells.

The sealed cavity 112 holds a colorless, transparent fluid 114 that is preferably biocompatible and whose index of refraction is about 1.40 to about 1.80 (e.g., about 1.46 to about 1.65). Suitable fluids include those with viscosities of about 20 centipoise to about 1000 centipoise, such as low-molecular-weight fluorocarbons and certain oils. When filled with the fluid 114, the pressure of the flexible membrane is about 2 mm mercury to about 100 mm of mercury (e.g., about 5 mm mercury to about 50 mm mercury) compared to a pressure inside a human eye of about 2 mm mercury to about 25 mm mercury.

The implantable ophthalmic device 100 also includes a pair of actuators 120 disposed about the circumference of the flexible membrane 116. When viewed along the optical axis of the device 100, the actuators 120 may appear to be rings or annular arcs concentric with the center of the variable lens element 110 (i.e., the optical axis). Applying an electromagnetic potential to the actuators 120 causes the actuators 120 to squeeze the circumference of the flexible membrane 116. This squeezing action compresses the peripheral portion of the flexible membrane 116, forcing the liquid 114 towards the center of the sealed cavity 112, which, in turn, causes the center of the flexible membrane 116 to bulge as shown in FIG. 1B. In other words, squeezing the periphery of the flexible membrane decreases the radius of curvature of the central portion of the flexible membrane 116. As understood by those of skill in the art, changing the radius of curvature of the flexible membrane 116 changes the optical power of the variable lens element 110. In some examples, the optical power of variable lens element 110 may change by about 0 Diopters to about 3.50 depending on the amount of force exerted by the actuators 120 on the flexible membrane 116.

In one example, each actuator 120 includes a layer of a substantially transparent ferromagnetic material (not shown) that is about 0.1 microns to about 2.0 microns in thickness (e.g, about 0.5 micron to about 1.5 microns in thickness) and about 0.1 mm to about 2.5 mm in width (e.g., about 0.1 mm to about 1.0 mm in width). Each layer of ferromagnetic material is in electrical contact with an electrode made of transparent, electrically conductive material (not shown), such as indium tin oxide, that functions as an electrode. Each electrode may be about 0.05 microns to 2 microns thick (e.g., about 0.1 microns to about 0.2 microns thick). The actuators 120 are operated by inducing magnetism in the ferromagnetic layers, thus causing the ferromagnetic layers to become attracted to each other such that they squeeze the edge of the flexible membrane 116. The amount of force exerted by the actuators 120 on the flexible membrane 116 (and, hence, the change in optical power) is continuously variable as a function of the electromagnetic potential applied to the actuators 120.

Other suitable actuators include micro-electro-mechanical systems (MEMS) devices and shape-memory devices. For instance, an actuator may include a C-shaped member that is made of shape-memory alloy and folded or bent around at least part of the circumference of the flexible membrane 116. Heating the C-shaped member (e.g., by running a current through it) causes the shape-memory alloy to reversibly change phase, which, in turn, causes the C-shaped member to change shape (e.g., to straighten out or to curl). As the C-shaped member changes shape, it either compresses or releases the edge of the flexible membrane 116, causing the optical power of the variable lens element to change as described above.

The variable lens element 110 is bonded to an optional flexible, hydrophobic static lens element 130 with a diameter of about 3.0 mm to about 7.0 mm (e.g., 5.0 mm to 6.0 mm). The static lens element 130 can be made of a biocompatible material, such as a hydrophobic cross-linked acrylic elastomer, in the form of a spherical or aspheric plano-convex lens with a fixed optical power of about 0 Diopters to about 35 Diopters (e.g., 12 Diopters to 30 Diopters, 16 Diopters to 26 Diopters, or any other value between 4 Diopters and 35 Diopters). If desired, the optical designs of the variable lens element 110 and the static lens element 130 can be optimized for best retinal image quality using an eye model, ensuring the elimination of optical discontinuities including, but not limited to discontinuities in sag, prism, or optical power.

The static lens element 130 has an elastic modulus that is substantially higher than the variable lens element's elastic modulus, which may be about 500 psi to about 700 psi. In some cases, the elastic modulus of the static lens element 130 is between about two times and about 1000 times greater than the elastic modulus of the variable lens element 110. For instance, the elastic modulus of the static lens element 130 may be about ten to fifty times greater than the elastic modulus of the variable lens element 110. (That is, the elastic modulus of the static lens element may be about 1000 psi to about 70,000 psi, e.g., about 5000 psi to about 35,000 psi.) Because it has a higher elastic modulus, the static lens element 130 is not deformed significantly by any squeezing force applied by the actuators 120. As a result, the squeezing force applied by the actuators 120 causes the free (i.e., unbonded) surface of the variable lens element 110 to moves toward the interface between the variable lens element 110 and the static lens element 130.

An illustrative implantable ophthalmic device may also include or be coupled to a sensor 140 that detects an accommodative stimulus, a controller or processor (not shown) that triggers the actuators 120 in response to a signal from the sensor, and a power source (not shown), such as a rechargeable lithium ion battery or a capacitor, that provides power to the actuators 120. Exemplary sensors, controllers, and power sources are described in greater detail below. In an illustrative example, the implantable ophthalmic device, sensor, controller, and power supply may be encapsulated in a hermetically sealed capsule as described below with respect to FIG. 6.

Figure 2:
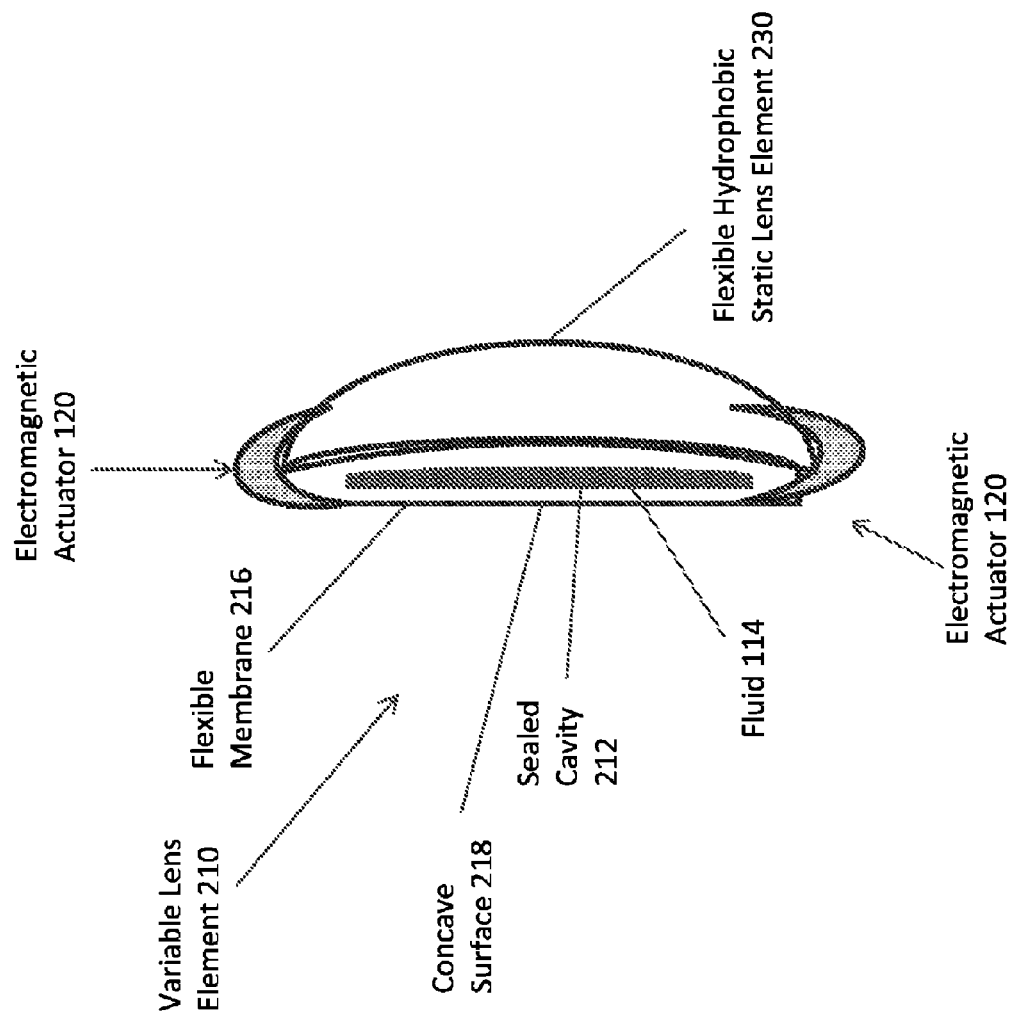
FIG. 2 is a side view of an alternative adaptive implantable ophthalmic device with a mechanically actuated fluid-filled membrane.

FIG. 2 shows an alternative implantable ophthalmic device 200 that includes a variable lens element 210 bonded to a biconvex or a plano-convex static lens element 230. The variable lens element 210 is a concave-convex lens element, or meniscus, whose concave surface 218 forms at least part of the anterior surface of the implantable ophthalmic device 200. The variable lens element 210 includes a meniscus liquid-filled capsule 216 that defines a sealed cavity 212 filled with transparent, colorless fluid 114. As described above with respect to FIGS. 1A and 1B, one or more actuators 120 along the circumference of the liquid-filled capsule 216 squeezes the edge of the capsule 216 in response to detection of an accommodative stimulus; this squeezing causes the capsule 216 to change shape (e.g., to bulge), which changes the optical power of the variable lens element 210. For example, at least a portion of the concave surface 218 of the capsule 216 may flatten out or even protrude away from the static lens element 230 when the actuators 120 compress the capsule 216. One advantage of using a meniscus-shaped variable lens element 210 is that the displacement of the movable surface (i.e., the concave surface) due to optical power adjustment is smaller for meniscus optics than for plano-convex optics.

Optical Power Variation by Fluid Phase Changes

FIGS. 3A and 3B show another alternative implantable ophthalmic device 300 containing a fluid 314 that can be switched between a first phase (FIG. 3A) and a second phase (FIG. 3B) whose molar volume is greater than that of the first phase. Heating or applying an electromagnetic potential (e.g., a voltage) to the fluid 314 causes the fluid 314 to switch from the first phase to the second phase. Switching the fluid 314 between phases causes at least a portion of the device's radius of curvature to change, which, in turn, yields a corresponding change in optical power of between about 0 Diopters to about 3.5 Diopters. In this example, the optical power of the implantable ophthalmic device 300 increases as the expanding fluid 314 inflates a portion of the device 300.

The implantable ophthalmic device 300 of FIGS. 3A and 3B includes a thin, rigid shell 302 with an edge thickness of about 0.1 mm to about 1.5 mm (e.g., about 0.3 mm to about 1.2 mm). The shell 302 may be shaped in the form of a plano-convex optic or a biconvex optic whose surfaces have the same or different radii of curvature of about 8.0 mm to about 20.0 mm (e.g., 10.0 mm, 12.5 mm, 15.0 mm, 17.5 mm, or any other value between 8.0 mm and 20.0 mm). Each surface of the shell 302 may have either a spherical curvature or an aspheric curvature. The shell 302 may also form a static optical element or include a separate static lens element 330 that provides a fixed optical power of about 0.00 Diopters to about 35.00 Diopters (e.g, about 12.00 Diopters to about 30.00 Diopters, or about 16.00 Diopters to about 26.0 Diopters).

The shell 302 has a thickness of about 100 microns to about 500 microns (e.g., about 100 microns to about 200 microns) and is made of biocompatible material, such as flexible plastic, mineral glass, $SiO_x$, or any other suitable material. It also defines an optical cavity 304 of about 5.0 mm to about 10.0 mm in diameter (e.g., about 5.0 mm to about 8.0 mm in diameter) and a volume of about 80 mm$^3$ to about 250 mm$^3$. The anterior surface of the shell 302 features a circular or elliptical aperture 306 of about 2.00 mm to about 5.00 mm (e.g., about 3.0 mm to about 4.5 mm) that connects the optical cavity 304 to the exterior of shell 302.

A colorless, transparent flexible membrane 316 is disposed within the optical cavity 304 and protrudes partially through the aperture 306 when inflated. The flexible membrane 316 has a thickness of about 5 microns to about 100 microns (e.g., about 10 microns to about 50 microns) and is made of a polyfluorocarbon or other suitable biocompatible material. The membrane 316 defines a sealed cavity 312 filled with fluid 314 that changes in molar volume (i.e., expands and contracts) in response to heat or voltage provided by one or more actuators, depicted in FIGS. 3A and 3B as transparent resistive electrodes 320 that cover at least part of the flexible membrane's outer surface.

A processor 360 coupled to a sensor 140 and a battery 350 controls the electrodes 320. When the sensor 140 detects an accommodative stimulus, it sends a signal to the processor 360. The processor 360 responds to the signal by running current supplied by the battery 350 through the electrodes 320 so as to heat the fluid 314, which undergoes a forward phase transition from a first phase to a second phase once it reaches a first phase transition temperature, which can be about 2° C. to about 10° C. above nominal body temperature (37° C.) (e.g., about 4° C. to about 8° C. above nominal body temperature). (Alternatively, the electrodes 320 may apply a voltage across the fluid 314 to induce the phase change via resistive heating of the fluid 314 or shifting of the fluid's phase transition temperature.) The fluid 314 is transparent and stable in both phases, but has a higher molar volume in the second phase; this increase in molar volume causes the flexible membrane 316 to increase in volume by about 0.20 mm$^3$ to about 0.50 mm$^3$ as described above and shown in FIG. 3B. The fluid 314 exhibits hysteresis: it undergoes a reverse phase transition (i.e., a transition from the second phase to the first phase) at a temperature that is different than the temperature of the forward phase transition.

In some examples, the fluid 314 includes a colorless, transparent liquid crystal material whose refractive index is about 1.40 to about 1.80 (e.g., about 1.46 to about 1.65). The fluid 314 may even include a mixture of liquid crystal materials. As understood by those of skill in the art, liquid crystal materials have different phases, each of which has a corresponding degree of order. The molar volume of the phases tends to increase with the degree of disorder; i.e., ordered phases have low volumes and disordered phases have high volumes. In general, smectic phases are highly ordered, nematic phases are partially ordered, and isotropic phases are disordered. One or more of these phases may be transparent, biocompatible, and have medium to low viscosity (e.g., less than 10,000 poise). Each phase may also have a different refractive index as well; the change in refractive index may further change the optical power of the implantable ophthalmic device 300.

A suitable liquid crystal material may undergo a first-order phase transition accompanied by a change in molar volume that ranges from about 0.1% to about 0.4% (e.g., about 0.15% to about 0.3%) between two transparent phases in response to heat or an applied voltage. As understood by those of skill in the art, a first-order phase transition under the Ehrenfest classification scheme is a phase transition that exhibits a discontinuity in the first derivative of the free energy with respect to some thermodynamic variable. Second-order phase transitions are continuous in the first derivative (the order parameter, which is the first derivative of the free energy with respect to the external field, is continuous across the transition), but exhibit discontinuity in a second derivative of the free energy. Liquid crystal materials exhibit complex phase diagrams featuring first- and second-order phase transitions. First-order phase transitions within the liquid crystalline domain are characterized by well-defined transition temperatures that may be modulated by application of pressure, or electric or magnetic fields.

For instance, a liquid crystal material may have a first-order phase transition (e.g., a transition from a nematic phase to an isotropic phase) that occurs close to but slightly above the ambient temperature inside the eye and is accompanied by a change in molar volume that can range from about 0.1% to about 0.3% (i.e., Aviv of about 0.001 to about 0.003). In one example, the liquid crystal material may undergo a phase transition from a low-volume smectic phase to a higher-volume nematic phase when heated by the electrodes 320 to a temperature of about 40° C. for about 0.1 seconds, causing the flexible membrane 316 to inflate. The liquid crystal material cools quickly to ambient temperature, where it remains in the nematic phase. Heating the nematic-phase liquid crystal material to a higher temperature (e.g., about 40° C. for about 0.1 seconds) causes the liquid crystal material to undergo a phase transition from the stable nematic phase to an unstable isotropic phase. As the isotropic-phase liquid crystal material cools to ambient temperature, it transitions again to the stable smectic phase. Alternatively, the liquid crystal material can be cooled (e.g., using a miniature thermo-electric cooler) below a phase transition temperature that is less than the eye's ambient temperature so as to change the optical power of the implantable ophthalmic device.

TABLE 1 shows the transition temperatures, transitional densities, and transitional volume changes for different liquid crystal materials in the homologous series of alkyl-cyanobiphenyl liquid crystals $C_nH_{2n+1}$PhPhCN (n=5 to 9). All the liquid crystal materials listed in TABLE 1 have nematic and isotropic phases, while the higher members with n=8 and n=9 also show smectic A phases. The nematic-to-isotropic phase transitions for n=7 and n=8 occur just above 37° C., which is the nominal temperature of a human body.

TABLE 1

Liquid Crystal Material Properties

| Liquid Crystal (R) | Transition Temperatures (° C.) | | Transitional Densities (g cm$^{-3}$) | | | Transitional Volume Change $\Delta v/v$ |
|---|---|---|---|---|---|---|
| | $T_S$ | $T_N$ | Smectic A | Nematic | Isotropic | |
| $C_5H_{11}$ (5 CB) | | 35.0 | | 1.01135 | 1.00933 | 0.00200 |
| $C_6H_{13}$ (6 CB) | | 29.4 | | 1.00336 | 1.00240 | 0.00096 |
| $C_7H_{15}$ (7 CB) | | 42.7 | | 0.98621 | 0.98406 | 0.00220 |
| $C_8H_{17}$ (8 CB) | 33.6 | 40.6 | 0.98955 | 0.98922 | | 0.00030 |
| | | | | 0.97996 | 0.97831 | 0.00170 |
| $C_9H_{17}$ (9 CB) | 47.7 | 49.5 | 0.97262 | 0.97224 | | 0.00040 |
| | | | | 0.96790 | 0.96434 | 0.00370 |

Figure 4:
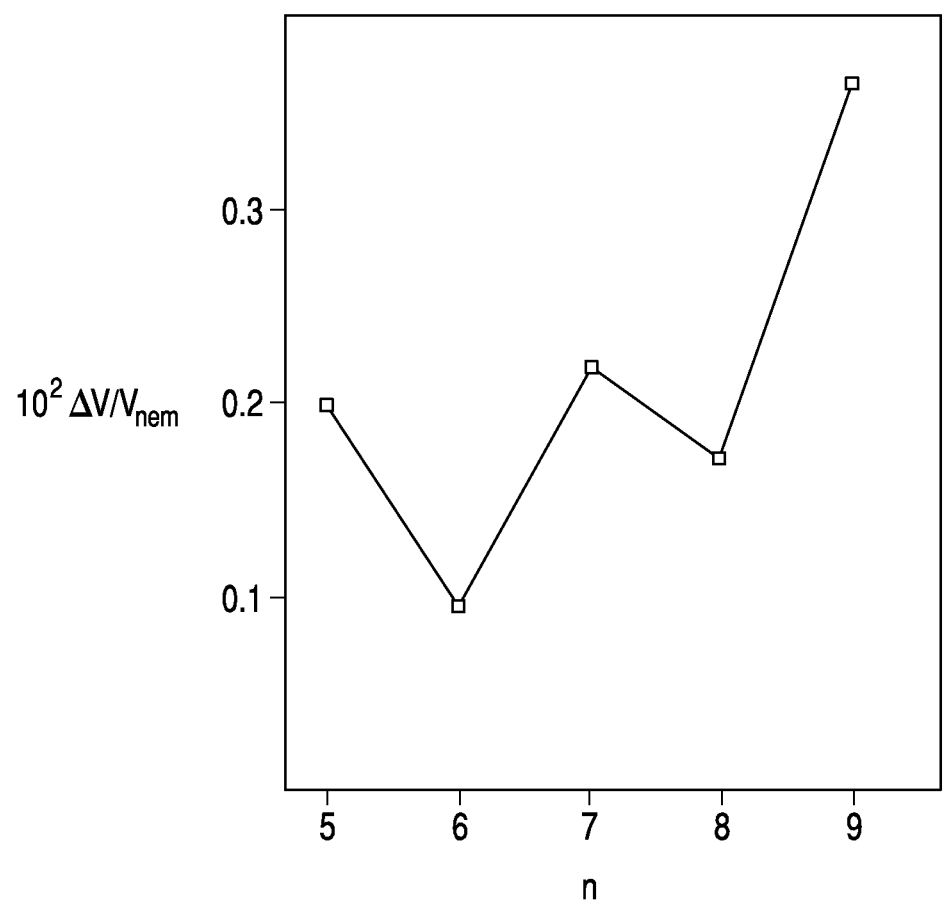
FIG. 4 is a plot of fractional volume change associated with the nematic-to-isotropic phase transition as a function of alkyl chain length for the homologous series of alkyl-cyano-biphenyls (n=5→9).

FIG. 4 is a plot of the fractional volume change for the nematic-to-isotropic phase transition as a function of n for the liquid crystal material in TABLE 1. The nematic to isotropic transitions are all very sharp—each occurs over less than 0.1° C.—but the transition from the smectic A phase to the nematic phase is less sharp (where applicable). FIG. 4 also shows an odd-even effect for members of the homologous series of alkyl-cyanobiphenyl liquid crystals: those members having an odd number of carbon atoms are more extended than those with an even number, and have a higher order parameter, which is an expression of the degree of order among molecules in the liquid crystal material. Thus, the relatively higher order of the odd members of the series results in a larger volume change at the nematic-to-isotropic transition.

Figure 5A:
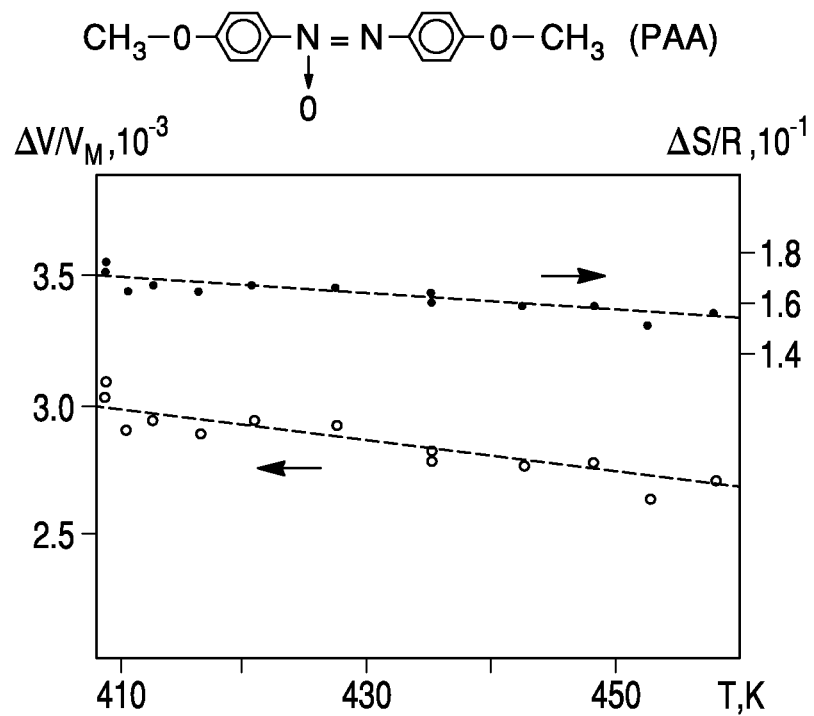
FIG. 5A is a plot of fractional volume change and fractional change in entropy versus temperature for para-azoxyanisole (PAA) liquid crystal material.

FIG. 5A is a plot of fractional volume change (left axis) and fractional change in entropy (right axis) as a function of temperature for para-azoxyanisole (PAA) liquid crystal material at high pressures. The upper dashed line represents the change in fractional volume and fractional entropy with increasing temperature as the PAA liquid crystal material undergoes a forward phase transition from a low-volume (relatively ordered) nematic phase to a high-volume (relatively disordered) isotropic phase. The lower dashed line represents the change in fractional volume and fractional entropy with decreasing temperature as the PAA liquid crystal material undergoes a reverse phase transition from the isotropic phase to the nematic phase. The different lines for the forward and reverse transitions indicate both hysteresis and a volume discontinuity as the PAA liquid crystal material switches between nematic and isotropic phases.

The phase of the liquid crystal material can also be changed by applying an electric or magnetic field to the liquid crystal material. Applying a voltage across the liquid crystal material can cause resistive heating of the liquid crystal material that drive the liquid crystal material across its phase transition temperature. Alternatively, or in addition, applying a voltage across the liquid crystal material may also modulate the phase transition temperature of the liquid crystal material so that the desired phase transition occurs at the ambient temperature inside the eye.

Figure 5B:
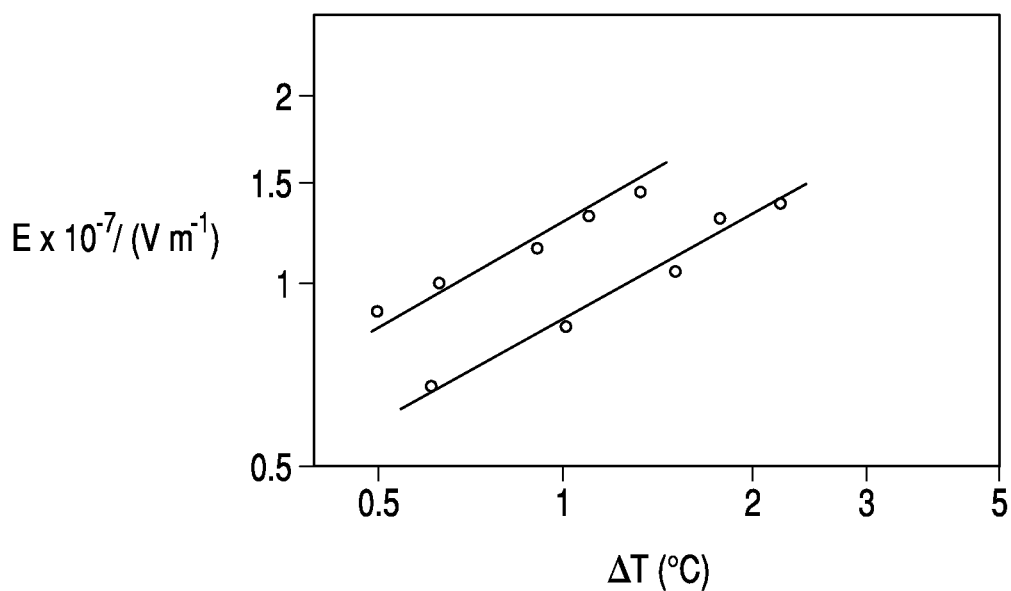
FIG. 5B is a log-log plot of the change in nematic-to-isotropic phase transition temperature versus electric field for two nematic cyano-biphenyl liquid crystal materials: (1) five carbon CB and (2) 6-CB.

FIG. 5B is a plot of the applied electric field versus the change in temperature of the nematic-to-isotropic phase transition for two different cyano-biphenyl liquid crystal materials: (1) 5-CB and (2) 6-CB. In both cases, increasing the strength of the electric field causes the temperature of the nematic-to-isotropic phase transition to increase. In one example, the electrodes 320 shown in FIGS. 3A and 3B may be configured to apply a voltage to liquid crystal material (fluid 314) in the sealed cavity 312 so as to change the phase of the liquid crystal material without changing the temperature of the liquid crystal material (or to prevent the liquid crystal material from changing phase at a given temperature). Applying an electromagnetic field to the liquid crystal material may also change a first-order phase transition to a second-order transition.

Encapsulated Implantable Ophthalmic Devices

Figure 6:
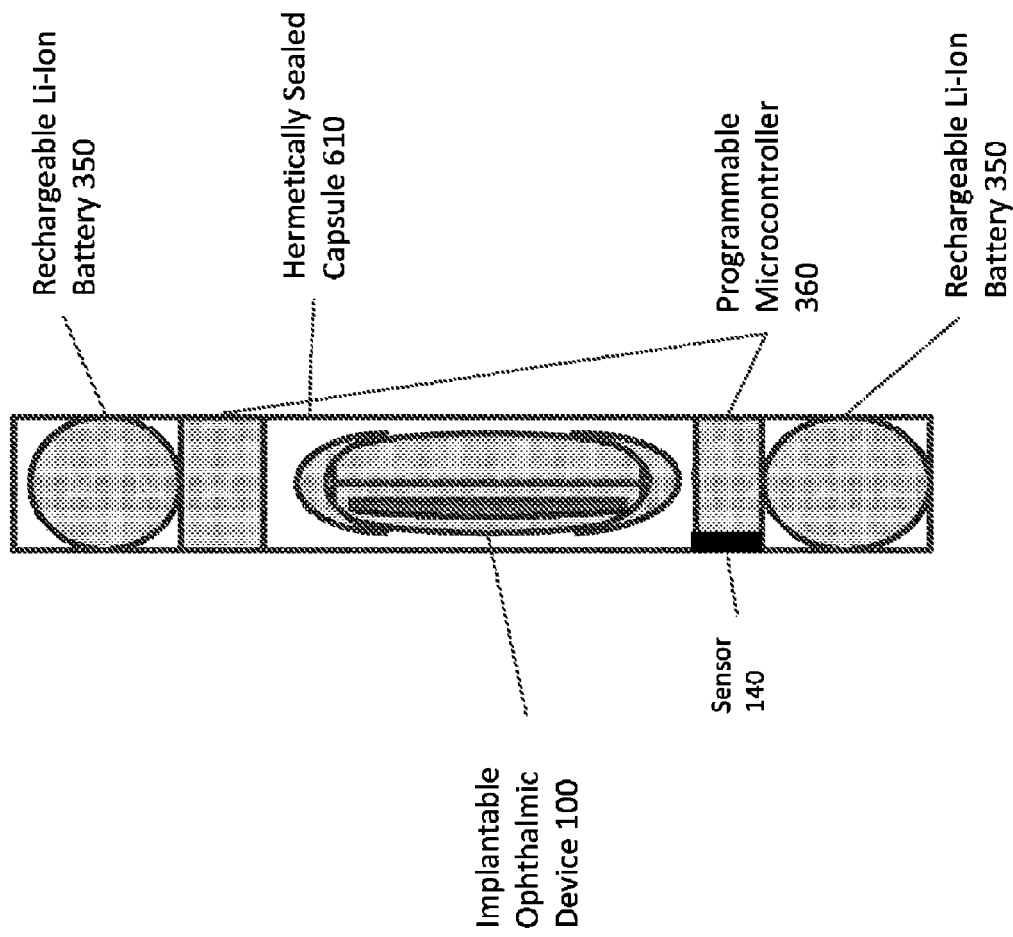
FIG. 6 is a side view of the adaptive implantable ophthalmic device encapsulated in a hermetically sealed capsule.

Illustrative implantable ophthalmic devices, including those shown in FIGS. 1-3, may be hermetically sealed in a capsule 610 along with a sensor 140, one or more batteries 350, and one or more controllers 360 for implantation in a mammalian eye as shown in FIG. 6. The capsule 610 may be formed of two or more glass plates, each of which has a thickness of about 25 microns to about 250 microns (e.g., about 25 microns to about 125 microns). The capsule 610 is filled with saline or some other suitable fluid in order to minimize reflections or loss of image quality resulting from internal reflections off the surfaces of the implantable ophthalmic device 100, sensor 140, batteries 350, and controllers 360. Next, the capsule 610 is sealed using laser fusion, laser welding, or any other suitable hermetic sealing process. The capsule 610 may be further encapsulated by a transparent, hydrophobic acrylic optical material that is biocompatible and foldable. When completely sealed, the capsule 610 can be about 3.5 mm to about 6.5 mm in length, about 3.0 mm to about 6.5 mm in width, and about 1.0 mm to 3.5 mm in thickness.

Alternatively, the capsule 610 may be formed of glass- or $SiO_x$-coated plastic, such as acrylic, polyimide, PMMA, PVDF, or any other suitable polymer or fluorocarbon. In some examples, the glass or $SiO_x$ coating is about 200 nm thick, and the plastic is about 5 microns thick to about 100 microns thick. The plastic is highly impermeable, as highly and moderately permeable plastics swell during use through absorption of moisture. (Some permeable plastics may absorb up to 5-6% moisture.) If the capsule absorbs too much moisture, it will swell enough to crack the coating.

Power Sources

As noted above, the actuators, sensor, and controller draw electrical power from a power supply, such as a solar cell, capacitor, or thin-film rechargeable battery like those manufactured by Excellatron, Wyon, or Front Edge. In FIGS. 3A, 3B, and 6, for example, a rechargeable battery 350 provides power for the actuator 320, sensor 140, and controller 360. Suitable power sources include rechargeable lithium-ion batteries with a minimum of 1,000 cycles of recharging, a diameter in the range about 0.8 mm to about 2.5 mm (e.g., about 0.8 mm to about 1.3 mm), and a thickness of about 500 microns to about 3.0 mm (e.g., about 0.7 mm to about 2.0 mm). If desired, the batteries may be recharged using an inductive antenna as described in PCT/US2011/040896 filed Jun. 17, 2011, and entitled, "ASIC Design and Function," and PCT/US2011/050533 filed Sep. 6, 2011, and entitled, "Installation and Sealing of a Battery on a Thin Glass Wafer to Supply Power to an Intraocular Implant," each of which is incorporated herein by reference in its entirety.

Thin-film rechargeable batteries are particularly well-suited for use in implantable ophthalmic devices because they can be cycled more 45,000 times, which could translate to a usable lifetime of 20-25 years in the lens or optic. Two thin film rechargeable batteries may be used and may stacked one atop the other. In this configuration, one of the batteries may be used for 20-25 years and the other battery may be switched to when the first battery is no longer operable. Alternatively, the other battery may be switched to by a signal sent remotely to the controller. This may extend the lifetime of the optic or lens to 40-50 years.

One or more light-sensitive cells, such as solar cells or photovoltaic cells, may also be used to supplement, augment, and/or obviate the need for a battery. The light-sensitive cell is located out of the user's line of sight of the user, e.g., peripheral to the margin of the pupil when partially dilated by darkness, but not fully dilated. The device may thus be charged by using an eye-safe laser capable of energizing the light-sensitive cell or cells.

Alternatively, the light-sensitive cell may be located in front of (closer to the cornea of the eye) and separately disposed from a portion of the iris of a user's eye. Thin electrical wiring may operably connect the solar cell to the controllers. The electrical wiring may pass through the pupil without touching the iris and operably connect to the implantable ophthalmic device. The solar cell may be large enough such that it supplies enough electrical power to obviate the need for a separate power supply. The thin electrical wiring may not conduct electricity and may have a form factor which has the appropriate tensile strength to hold the solar cell in place. In some configurations, one or more small holes may be made in the iris by an ophthalmic laser such that the thin electrical wiring connects the solar cell to the implantable ophthalmic device.

Programmable Controller(s)

The controlling system comprises at least one programmable controller or processor (e.g., as shown in FIGS. 3A, 3B, and 6) that receives and processes signals from one or more sensors to determine when the patient is viewing an near or intermediate object. In other words, the controlling system monitors and responds to indications accommodative stimuli. The controller may also receive energy form an antenna and transform the received energy into a voltage suitable for re-charging the power supply. It may also step up or step down a voltage from the power supply (e.g., 1.6 Volts from a lithium-ion battery) into a voltage suitable for driving the actuators described above. In addition, the controller may also maintain a memory, or data register, that records sensor data and stores instructions for processing the sensor data. The controller may also update the memory and provide an uplink via the antenna to a host computer.

In some embodiments, the controller may include one or more application-specific integrated circuits (ASICs) as disclosed in PCT/US2011/040896 filed Jun. 17, 2011, and entitled, "ASIC Design and Function," which is incorporated herein by reference in its entirety. The first ASIC, which operates at relatively low voltage, e.g., about 4 V, provides functions such as data storage (memory), battery charging, etc. The second ASIC, which operates at relatively high voltage, e.g., 5-11 V, includes a charge pump that steps up the voltage from a power supply, such as a 1.4 V lithium-ion battery, to the 5-11 V actuation voltage of an electro-active cell. Because most of the electronics operate at low voltage, they consume less power, which increases the useful battery life (and the useful life of the device itself), e.g., to about twenty years or more. In addition, charge pumps consume less power and require less area (i.e., they have smaller footprints) than other DC-DC power converters, which makes it possible to reduce the size and power consumption of the second ASIC. Charge pumps also do not require the expensive inductors or additional semiconductors used in other DC-DC converters.

In some exemplary devices, the functions (and associated functional components) are partitioned among the first (low-voltage) ASIC and second (high-voltage) ASIC as follows. The first ASIC includes the functional blocks that are powered by a radio-frequency (rf) field, including an rf communication section (including an antenna), parts of the power management, and the battery charging. The second ASIC includes the functional blocks that are associated with therapy (variation in optical power). These therapy functional blocks may be powered by one or more batteries. The first and second ASICs communicate via a serial communication interface, which may be housed on the second ASIC and powered through the first ASIC.

The first ASIC regulates the second ASIC. In other words, the first ASIC controls the second ASIC's operational state by initiating "wake-up," i.e., by causing the second ASIC to transition from an idle (sleep) state in which the second ASIC does not actuate or power the electro-active element or consume much power to an operational state in which the second ASIC steps up the battery voltage and/or actuates or powers the electro-active element. By controlling the operating state of the second (high-voltage) ASIC with the first (low-voltage) ASIC, the ophthalmic device consumes less power than other ophthalmic devices that offer similar functionality to the patient.

The second ASIC may also include a battery voltage level monitor which samples the battery voltage in a periodic fashion while the second ASIC is in both the idle and operational states. When the battery level monitor senses that the battery voltage has dropped below a predetermined threshold, e.g., due to self-discharge, a switch (e.g., a latch element, such as an R-S flip-flop) in the second ASIC opens, disconnecting the second ASIC from the battery to stop further discharge of the battery. Other features for reducing current consumption (and extending the device lifetime) include operating the ASICs at a low clock frequency, making as few gate state transitions as possible, and intermittently enabling analog functional sections whenever possible.

Sensors for Detecting Accommodative Stimuli

As described above and shown in FIGS. 1-3 and 6, an inventive implantable ophthalmic device may include one or more sensors that produce electromagnetic or electrochemical signals in response to accommodative stimuli (defined below). In one embodiment, the sensor includes at least two silicon photocells comprising a layer of polycrystalline or amorphous silicon deposited on the inner surface of a capsule (e.g., capsule 610 in FIG. 6). The photocells may be about 0.05 mm by 0.05 mm or a 50-micron circle, ranging from about 0.02 mm by about 0.02 mm to about 1.0 mm by about 1.0 mm. Alternatively, the sensor(s) may include one or more piezoelectric elements that can sense constriction and dilation of ciliary processes. Still other sensors may include one or more motion sensors or accelerometers that detect motions of the eye. These motions can be analyzed by the controller to determine incidences of convergence. One or more sensors may be deployed to enhance accuracy of deployment of the variable optical power provided by the implantable ophthalmic device.

In some inventive implantable ophthalmic devices, the sensor system includes at least two sensors for distinguishing accommodative stimuli from changes in ambient lights levels and task-induced changes in the pupil diameter. When implanted, the first sensor is disposed completely within the pupil; even when fully constricted, the pupil does not occlude the first sensor, allowing the sensor to make precise measurements of ambient luminous flux levels. The second sensor is disposed, when implanted, such that the pupil occludes part of the second sensor's active area(s) as the pupil dilates and constricts. As a result, the second sensor measures both ambient luminous flux and pupil diameter. A processor estimates the pupil diameter from the measurements and determines whether the pupil is changing in diameter in response to accommodative stimuli or other factors by comparing the estimated pupil diameter and measured ambient light levels to predetermined values. The sensor system sends a signal to an optical component, which in turn can respond by changing optical power to focus for near vision upon detection of accommodative stimuli. Further details of suitable sensors can be found in U.S. Patent Application Publication No. 2010/0004741 filed Jul. 2, 2009, and entitled, "Sensor for Detecting Accommodative Trigger," and in PCT/US2011/051198 filed Sep. 12, 2011, and entitled, "Method and Apparatus for Detecting Accommodations," both of which are incorporated herein by reference.

As used herein, "ambient light" means light exterior to the eye. In some embodiments, ambient light refers more specifically to the light exterior to, but near or adjacent to the eye, e.g., light near the corneal surface. Ambient light can be characterized by variables such as the amount of light (e.g., intensity, radiance, luminance) and source of light (including both natural sources, e.g., sun and moon, as well as artificial sources such as incandescent, fluorescent, computer monitors, etc.).

As used herein, "accommodative response" refers to one or more physical or physiological events that enhance near vision. Natural accommodative responses, those that occur naturally in vivo, include, but are not limited to, ciliary muscle contraction, zonule movement, alteration of lens shape, iris sphincter contraction, pupil constriction, and convergence. The accommodative response can also be an artificial accommodative response, i.e., a response by an artificial optical component. Artificial accommodative responses include, but are not limited to, changing position, changing curvature, changing refractive index, or changing aperture size.

The accommodative response (also known as the accommodative loop) includes at least three involuntary ocular responses: (1) ciliary muscle contraction, (2) iris sphincter contraction (pupil constriction increases depth of focus), and (3) convergence (looking inward enables binocular fusion at the object plane for maximum binocular summation and best stereoscopic vision). Ciliary muscle contraction is related to accommodation per se: the changing optical power of the lens. Pupil constriction and convergence relate to pseudo-accommodation; they do not affect the optical power of the lens, but they nevertheless enhance near-object focusing. See, e.g., Bron A J, Vrensen G F J M, Koretz J, Maraini G, Harding 11.2000. The Aging Lens. Ophthalmologica 214: 86-104.

As used herein, "accommodative impulse" refers to the intent or desire to focus on a near object. In a healthy, non-presbyopic eye, the accommodative impulse would be followed rapidly by the accommodative response. In a presbyopic eye, the accommodative impulse may be followed by a sub-optimal or absent accommodative response.

As used herein, "accommodative stimulus" is any detectable event or set of circumstances correlated to accommodative impulse or accommodative response. In the devices described herein, when an accommodative stimulus is detected by the sensor system, the sensor system preferably transmits a signal to an optical component, which in turn responds with an artificial accommodative response. Exemplary accommodative stimuli include, but are not limited to, physiological cues (such as pupil constriction and other natural accommodative responses) and environmental cues (such as ambient lighting conditions).

The following applications are incorporated herein by reference in their entireties:

U.S. Pat. No. 7,926,940 to Blum et al., issued Apr. 19, 2011, and entitled, "Advanced Electro-Active Optic Device";

PCT/US2011/038597 filed May 31, 2011, and entitled, "Intermediate Vision Provided by an Aspheric IOL with an Embedded Dynamic Aperture";

PCT/US2011/040896 filed Jun. 17, 2011, and entitled, "ASIC Design and Function";

PCT/US2011/041764 filed Jun. 24, 2011, and entitled, "Use of Non Circular Optical Implants to Correct Aberrations in the Eye";

U.S. Patent Application Publication No. 2010/0004741 filed Jul. 2, 2009, and entitled, "Sensor for Detecting Accommodative Trigger";

U.S. Patent Application Publication No. 2011/0015733 filed Jul. 14, 2010, and entitled, "Folding Designs for Intraocular Lenses";

PCT/US2011/050533 filed Sep. 6, 2011, and entitled, "Installation and Sealing of a Battery on a Thin Glass Wafer to Supply Power to an Intraocular Implant"; and PCT/US2011/051198 filed Sep. 12, 2011, and entitled, "Method and Apparatus for Detecting Accommodations."

CONCLUSION

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An implantable ophthalmic device comprising:
a lens comprising:
 a flexible membrane defining a sealed cavity; and
 a fluid disposed within the sealed cavity;
a sensor configured to detect an accommodative stimulus;
an actuator disposed outside the sealed cavity and at a circumferential edge of the flexible membrane, wherein the actuator is configured to apply a compression force directly to the flexible membrane and thereby alter a shape of the flexible membrane so as to change an optical power of the lens; and
a processor operably coupled to the sensor and configured to trigger the actuator to apply the compression force in response to the detected accommodative stimulus,
wherein the sensor is configured to detect a ciliary process and to provide a signal to the processor related to the detection of the ciliary process.

2. The implantable ophthalmic device of claim 1 wherein the flexible membrane forms an aspheric lens element having a negative spherical aberration.

3. The implantable ophthalmic device of claim 1 wherein the flexible membrane has a thickness of about 2 microns to about 100 microns.

4. The implantable ophthalmic device of claim 1, the flexible membrane further comprising a circumferential bonded zone, wherein the circumferential bonded zone has a thickness of 0.5 microns to 5 microns.

5. The implantable ophthalmic device of claim 1 wherein the pressure inside the flexible membrane is 2 mm Hg to 50 mm Hg.

6. The implantable ophthalmic device of claim 1 wherein the fluid has a refractive index of 1.40 to 1.80.

7. The implantable ophthalmic device of claim 1 wherein the fluid has a refractive index of 1.46 to 1.65.

8. The implantable ophthalmic device of claim 1 wherein the flexible membrane forms a variable lens with a first elastic modulus, and wherein the lens further comprises:
a static lens element in optical communication with the flexible membrane, the static lens element having a second elastic modulus greater than the first elastic modulus.

9. The implantable ophthalmic device of claim 8 wherein the static lens element has an optical power of 4 Diopters to 30 Diopters.

10. The implantable ophthalmic device of claim 8 wherein the second elastic modulus is at least two times greater than the first elastic modulus.

11. The implantable ophthalmic device of claim 8 wherein the second elastic modulus is ten times to fifty times greater than the first elastic modulus.

12. The implantable ophthalmic device of claim 8 wherein the second elastic modulus is no more than one-thousand times greater than the first elastic modulus.

13. The implantable ophthalmic device of claim 1 wherein the actuator is configured to elastically deform at least part of a circumferential portion of the flexible membrane so as to change a radius of curvature of at least part of the flexible membrane to provide the change in optical power.

14. The implantable ophthalmic device of claim 1 wherein the actuator changes the optical power of the lens by up to 3.5 Diopters.

15. The implantable ophthalmic device of claim 1 further comprising:
a sealed housing that encloses the lens and the actuator; and
another fluid, contained within the sealed housing, to reduce reflection from components within the housing.

16. The implantable ophthalmic device of claim 15, further comprising a power supply configured to power the actuator, and wherein the sealed housing further encloses the sensor, the processor and the power supply.

17. The implantable ophthalmic device of claim 1, wherein the flexible membrane includes a circumferential bonded zone defining the sealed cavity.

18. The implantable ophthalmic device of claim 1, wherein the actuator is configured to apply the compression force directly to the flexible membrane by squeezing a circumference of the flexible membrane.

19. An implantable ophthalmic device comprising:
a sealed housing encapsulating:
 a flexible lens element defining a sealed cavity;
 a fluid disposed within the sealed cavity;
 a sensor configured to detect an accommodative stimulus;
 an actuator disposed outside the sealed cavity and at a circumferential edge of the flexible membrane, wherein the actuator is configured to compress at least a peripheral portion of the flexible lens element so as to change an optical power of the ophthalmic; and
 a processor operably coupled to the sensor and configured to trigger the actuator to apply the compression force in response to the detected accommodative stimulus,
 wherein the sensor is configured to detect a ciliary process and to provide a signal to the processor related to the detection of the ciliary process.

20. The implantable ophthalmic device of claim 19, further comprising
a static lens element encapsulated by the sealed housing.

* * * * *